(12) United States Patent
Chan (10) Patent No.: US 10,302,546 B2
(45) Date of Patent: May 28, 2019

(54) MICROPARTICLE MULTIPLEXING

(71) Applicant: DNA Medicine Institute, Inc., Cambridge, MA (US)

(72) Inventor: Eugene Y. Chan, Boston, MA (US)

( * ) Notice: Subject to any disclaimer, the term of this patent is extended or adjusted under 35 U.S.C. 154(b) by 381 days.

(21) Appl. No.: 14/682,010

(22) Filed: Apr. 8, 2015

(65) Prior Publication Data

US 2015/0285729 A1  Oct. 8, 2015

Related U.S. Application Data

(60) Provisional application No. 61/977,041, filed on Apr. 8, 2014.

(51) Int. Cl.
  *G01N 15/14*   (2006.01)
  *G01N 15/02*   (2006.01)

(52) U.S. Cl.
  CPC ..... *G01N 15/1434* (2013.01); *G01N 15/0205* (2013.01); *G01N 15/1429* (2013.01); *G01N 15/1459* (2013.01); *G01N 2015/1493* (2013.01); *Y10T 428/2982* (2015.01)

(58) Field of Classification Search
  None
  See application file for complete search history.

(56) References Cited

U.S. PATENT DOCUMENTS

2011/0136104 A1* 6/2011 Pregibon .............. C12Q 1/6851
                                                      435/6.12
2012/0088691 A1*  4/2012 Chen ........................ B01L 7/52
                                                      506/12

OTHER PUBLICATIONS

Hwang et al (2009 JACS 131:4499-504).*
Hwang et al (2009 JACS 131:4499-504 supporting information).*

* cited by examiner

*Primary Examiner* — Christopher M Gross
(74) *Attorney, Agent, or Firm* — Danielson Legal LLC (57) ABSTRACT

Multiplexing microparticles by measurement of particle length and dye. Utilization of length-based measurements in combination with dye concentrations to attain multiplexing for bioassays.

17 Claims, 7 Drawing Sheets

MICROPARTICLE MULTIPLEXING

CROSS-REFERENCE TO RELATED APPLICATIONS

The present application claims the benefit of U.S. provisional application No. 61/977,041, filed on Apr. 8, 2014, the entire disclosure of which is incorporated by reference as if set forth in its entirety herein.

FIELD

The invention relates to the multiplexing of microparticles by length and dye intensity and, in particular, to the multiplexing of hydrogel microparticles that are fabricated by photolithographic approaches.

BACKGROUND

Assay multiplexing is of great interest and utility in the biomedical field. In particular, there is a need to measure multiple analytes in a given sample. This leads to analysis of more information for a particular sample, allowing greater utility in the diagnosis and identification of important biological markers in a given sample.

Bead-based multiplexing of bioassays is a common approach to sample multiplexing. For instance, it is known to use fluorescent beads that are dyed for multiplexing based on the amount of dye in the bead for identifying the sample. A bead that has low fluorescence in one color and high fluorescence in a second color can be readily distinguished in a multiplexed manner. The second color can then be utilized for measurement of the desired analyte.

Other permutations of bead-based multiplexing include the use of quantum dots for coding multiple colors in a microparticle. In this approach, quantum dots, which have sharp spectral emission profiles, can be mixed together in a microsphere. Ratios of the spectral emissions of the various colors allow for identification of the particle of interest. Since quantum dots have narrow emission profiles, several colors can be mixed together to allow for a significant level of multiplexing.

Hydrogel microparticles have been multiplexed by the addition of a simplified barcode to the header of the microparticle. Hydrogel microparticles can also have multiple elements, by where intensity coding of the uniform elements allows for multifunctional coding. Both barcodes on the header and within the microparticles lead to a unique intensity versus time profile signature on every microparticle.

Other types of coded microparticles include sub-micrometer metallic barcodes, 2D hydrogel barcodes, and one-dimensional barcodes. Glass microparticles can be fabricated to generate a 1D diffraction pattern that uniquely identifies the particles. Most of these methods require sophisticated imaging and decoding algorithms.

Hydrogel microparticles are well suited for biological assays and multiplexing. For instance, PEG microparticles have low autofluorescence, are porous, and can have different functionalities. In particular, PEG with reactive acrylate groups can be utilized to form hydrogel particles using ultraviolet (UV) exposure. PEG microparticles thus have desirable attributes for biological applications. PEG microparticles are advantaged over conventional polymeric (polystyrene, latex, etc.) particles in that they are porous, have low autofluorescence, and low non-specific binding.

PEG particles are readily formed by UV curing of acrylate functionalized PEG. PEG-monoacrylate (PEGMA) and PEG-diacrylate (PEGDA) are common forms of UV curable PEG. This involves the use of a photoinitiator with an acrylate functionalized PEG mixture. Exposure to UV leads to the initiation of the reaction and thus the formation of the particles.

Monodisperse PEG microspheres can be formed by droplet generation inside a microfluidic device. Hexadecane, which is immiscible with the PEG solution, is utilized as the sheath and a mixture of PEGDA and photoinitiator is the aqueous phase. The surface tension of the PEGDA mixture leads to formation of microspheres as the PEGDA stream is focused by the hexadecane phase. A surfactant in the hexadecane helps control the size of the droplets being formed. The hexadecane and PEGDA solutions are in a polydimethylsiloxane (PDMS) microfluidic device. The droplets are photocured by UV light to form stable particles that can be collected and utilized for downstream applications.

Diverse planar PEG microparticles can be synthesized by stop-flow or continuous flow lithography. In this approach, the shape of the PEG particles is controlled by a photomask placed at the field stop position of the microscope. UV light passing through the photomask is projected onto a flowing stream or stopped stream of PEGDA and photoinitiator mixture. The solution is cured by the UV light in the shape of the photomask. Different shapes have been fabricated: barcodes, circles, triangles, and rectangles. One of the advantages of this approach is that the shape is directly controlled by the photomask. Furthermore, the particle size and shape will be uniform. The throughput of particle production, however, will be lower than that of the droplet formation method. An additional advantage of PEG microparticles synthesized by either stop-flow or continuous flow lithography is that multiple laminar flow streams can be co-polymerized together to form multiple elements.

PEG microparticles on glass slides have also been synthesized. These PEG microparticles are formed by placing a droplet of the PEGDA and photoinitiator solution on a PDMS-coated glass slide and then exposing to UV light through a photomask. The shape of the photomask is projected onto the solution on the PDMS slide. The polymerized particles are flushed from the slide. This approach avoids the need for microfluidic channels, pumps, and fluid control. It represents a very simple method of producing uniform microparticles.

The flexibility of hydrogel particle fabrication lends itself readily to multiplexing. Because of this, numerous complex methods employing 1D and 2D can be readily implemented, but these may not be the best or most simple solutions. While 1D and 2D barcodes can lead to high levels of multiplexing, in practice, this is not necessarily required. Based on the complexity of these approaches, there is a need for increased simplicity in multiplexing.

SUMMARY

Embodiments of the present invention generally involve the addition of a length scale to hydrogel microparticles, which adds an additional parameter that can be leveraged to multiplex particles. Conventional polymeric beads do not have a length scale. The additional use of fluorescent dyes for coding allows for significant multiplexing of hydrogel microparticles.

In one aspect, embodiments of the present invention relate to a microparticle comprising at least one element, wherein each element has its own length and its own dye concentration, and wherein the microparticle is elongated.

In one embodiment, each of the at least one elements incorporates a different fluorescent dye. In one embodiment, the microparticle is fabricated substantially from polyethylene glycol. In one embodiment, the length of each of the at least one elements is at least the length required for a reader to identify a change in the element. The microparticle may be, for example, rectangular or cylindrical in shape.

In another aspect, embodiments of the present invention relate to a method for conducting an assay. The method includes introducing at least one microparticle into a sample, the microparticle having at least one element, wherein each element has its own length and its own dye concentration and the microparticle is elongated; and scanning the at least one microparticle with a laser.

In one embodiment, scanning the at least one microparticle with a laser determines the length of the at least one microparticle, and the method further comprises integrating the scanning measurement to determine burst intensity and grouping the microparticle by its length and burst intensity. In one embodiment, the method further includes decreasing the velocity of the at least one microparticle. In one embodiment, the method further includes increasing the sampling rate of the scanning. In one embodiment, each of the at least one elements incorporates a different fluorescent dye. The microparticle may be, for example, rectangular or cylindrical in shape. In one embodiment, the grouping of the microparticles is based on k-means clustering.

In still another aspect, embodiments of the present invention relate to an assay system comprising a source of elongated microparticles, each microparticle having at least one element, wherein each element has its own length and its own dye concentration; and a laser for scanning the microparticles.

In one embodiment, the system further includes a processing unit configured to control the laser to determine the length of at least one microparticle; integrate the scanning measurements to determine burst intensity; and group the microparticles by their length and curst intensity. In one embodiment, the system further includes means for decreasing the velocity of the microparticles. In one embodiment, the processing unit may be configured to increase the sampling rate of the scanning. In one embodiment, each of the at least one elements of the microparticles incorporates a different fluorescent dye. The microparticles may be, e.g., rectangular or cylindrical in shape.

The foregoing and other features and advantages of the present invention will be made more apparent from the descriptions, drawings, and claims that follow. One of ordinary skill in the art, based on this disclosure, would understand that other aspects and advantages of the present invention exist.

BRIEF DESCRIPTION OF DRAWINGS

In the drawings, like reference characters generally refer to corresponding parts throughout the different views. The drawings are not necessarily to scale, emphasis instead being placed on the principles and concepts of operation.

DETAILED DESCRIPTION

Embodiments of the present invention relate to an approach for multiplexing microparticles utilizing the length of various elements of the microparticles in combination with fluorescence intensity measurements. This approach is that it is simple, easily implementable, and matches the practical needs of the user.

Length is one of the parameters of a microparticle. In particular, length can be measured using flow cytometry, laser-induced fluorescence, or imaging. Imaging is not the most desirable option because of the complexity of image analysis. Instead, flow cytometry and laser-induced fluorescence give rise to intensity versus time data traces that can readily be measured by a single detector. In cytometry, the signal can be based off the fluorescence or scatter channels.

For measurement of length, the number of resolvable steps in the measurements determines the level of multiplexing available based on the length measurement. For instance, if 10 steps can be resolved, then based on length measurement alone 10-plex multiplexing can be attained.

In cytometry measurements, the length resolution is based on the velocity of the particle and the sampling rate of the detector. This results in the number of time bins of signal per particle. The greater the number of time bins per particle, the greater the resolution of different particle lengths.

Similarly, various dye concentrations can be incorporated into the microparticles. In this manner, the precision of the dye concentration and the dynamic range of the detector dictates the level of dye-based multiplexing. For instance, the ability to readily resolve five different dye concentrations results in 5-plex multiplexing and ten dye concentrations in 10-plex multiplexing. More than one fluorescent dye can be incorporated into individual microparticles to further increase the level of multiplexing. If the scatter channel on the cytometer is utilized, various granular, scattering agents can be included to make use of the scatter channels for multiplexing.

The total level of multiplexing is determined by the total number of combinations of length and dye intensity measurements. This is the product of the number of resolved steps for the length and dye. This can be summarized by:

$$C = n_l n_{d1} n_{d2} \ldots n_{di} \qquad \text{(Eq. 1)}$$

where C is the total number of combinations, $n_l$ is the number of resolvable discrete lengths, $n_{d1}$ is the number of resolvable dye 1 concentrations, $n_{d2}$ is the number of resolvable dye 2 concentrations, and $n_{di}$ is the number of resolvable dye i concentrations. Using this formula, 10 resolvable lengths and 5 resolvable dye 1 and dye 2 concentrations results in a total of 250 combinations, which is a high level of multiplexing.

Figure 1:
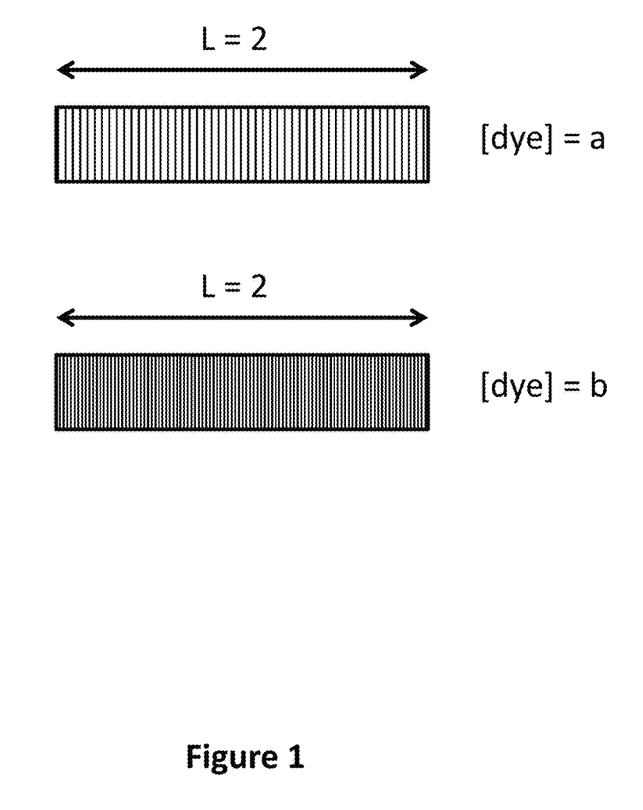
FIG. 1 shows one-element microparticles differentiated by dye concentration in accord with the present invention.

FIG. 1 is a depiction of hydrogel microparticles having length L=2 and coded by two different fluorescent dye concentrations, [dye]=a and [dye]=b. Per Eq. 1, these microparticles have two combinations.

Figure 2:
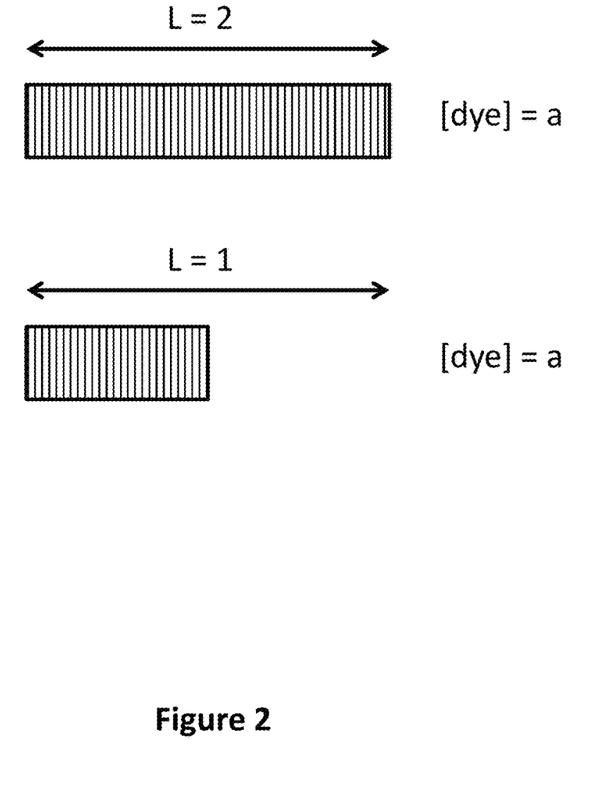
FIG. 2 shows one-element microparticles differentiated by length in accord with the present invention.

FIG. 2 is a depiction of hydrogel microparticles having different lengths L=1 and L=2, The dye concentration ([dye]=a) is the same in both, i.e., the particles are differentiated by their length L. Per Eq. 1, these microparticles have two combinations.

Figure 3:
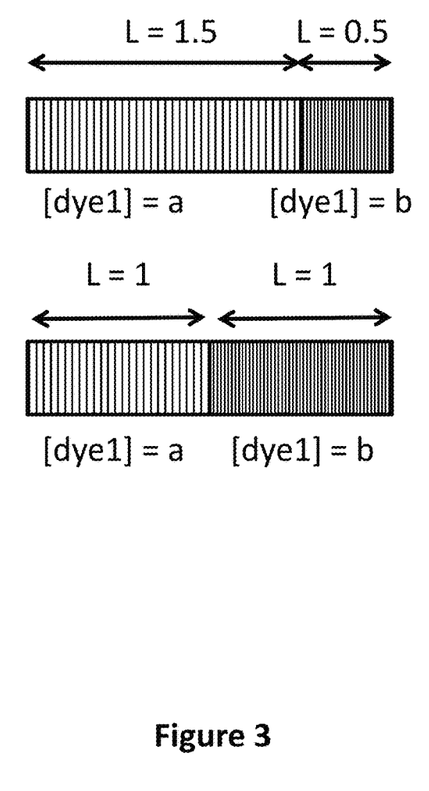
FIG. 3 shows two-element microparticles differentiated by both length and dye concentration in accord with the present invention.

FIG. 3 is a depiction of two-element hydrogen microparticles having different length elements and different dye concentrations. The top microparticle has one element with L=1.5 and a second element with L=0.5. Both elements have different dye concentrations, [dye1]=a and [dye1]=b. The bottom microparticle has one element with L=1 and another with L=1. Both elements have different dye concentrations, [dye1]=a and [dye1]=b. The microparticles are differentiated by the length of their elements, although the total length of the microparticles is the same. Per Eq. 1, these microparticles have eight combinations.

Figure 4:
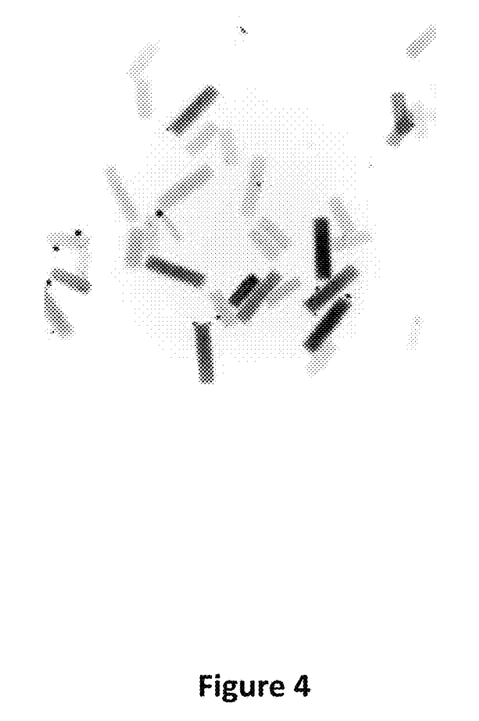
FIG. 4 is a photograph of one-element microparticles that are multiplexed by length and dye concentration in accord with the present invention.

FIG. 4 is a photograph of one-element microparticles where each element has one of two different lengths, L=1.5 or L=0.5, and one of two different dye concentrations, [dye1]=a or [dye1]=b. Per Eq. 1, these microparticles have four combinations.

One of the advantages of this invention is the large level of multiplexing attained using this approach. The number of resolvable length steps can be increased by changing particle length, increasing the sampling rate, decreasing the particle velocity, or generally increasing the number of time bins per particle.

The particle velocity distribution is typically important as well. It is preferable that individual particles have approximately the same velocity. In conventional flow cytometry, this is accomplished using flow focused streams that confine the analyzed sample to the center of the flowing stream.

Regular microspheres typically use two dyes to attain 25 to 30-fold multiplexing. In order to introduce more dyes and achieve higher levels of multiplexing, additional detectors are usually required. The use of a length measurement in addition can reduce the number of detectors needed for coding, thus freeing up detectors for assay measurements.

In one embodiment, the aforementioned hydrogel microparticles are fabricated in rectangular shapes by stop-flow or continuous-flow lithography. In stop-flow lithography, the PEG mixture is introduced into a microfluidic device with a straight channel and a depth consistent with the desired particle height. With the use of a 3-way valve and an electronically controlled shutter, the flow of the PEG mixture is stopped and the shutter is opened, allowing UV light to go through a photomask to pattern the PEG pre-polymer mixture. The flow is turned back on to move the polymerized particles downstream, allowing the cycle to be repeated again. The polymerization is performed on a Zeiss Axio Observer inverted microscope with a field stop position for the photomask, which is designed in AutoCAD and printed on a high-resolution printer (CAD/ART Services, OR). Exposure times are on the order of 50-100 ms, depending on the strength of the arc lamp and the number of hours on it. The stop-flow lithography approach provides lower throughput than droplet formation, but offers the advantage of providing different shapes for multiplexing.

In another embodiment, the hydrogel microparticles are fabricated using a slide-based method, which requires only a UV light source and no pumps or fluidics. The PEG prepolymer mixture is dropped onto a glass slide coated with cured PDMS. It is spread by placing a PDMS-coated photomask on top of it. UV light is transmitted through the photomask at 300 mW/cm$^2$ to cure the particles. The final hydrogel particles are obtained by flushing the PDMS-coated glass slide and the photomask to release the microparticles. The particles are washed to remove any unreacted molecules from the particles and resuspended in the reaction buffer of choice.

The prepolymer mixture for synthesis of the microparticles includes the use of poly(ethylene glycol) diacrylate (PEG-DA, $M_n$=700), distilled water, 2-hydroxy-2-methylpropiophenone photoinitiator, and methacryloxyethyl thiocarbamoyl rhodamine B. Typically, the PEG-DA concentration can range from 10-90%, the photoinitiator from 1-10%, and the fluorescent dye in the 1-1000 μM range. Solutions are prepared in the dark since they are light-sensitive. Other types of PEG can be utilized including poly(ethylene glycol) monoacrylate (PEG-MA) and also various molecular weights of PEG-DA and PEG-MA. Different types of photoinitiators and fluorescent dyes can be utilized. The particles are collected, centrifuged at 2000×g, and washed with the desired buffer.

Different methods of functionalization of the microparticles can be utilized. This includes the incorporation of nucleic acids and antibodies. For the incorporation of nucleic acids, an acrydite group coupled with the nucleic acid can be utilized (Integrated DNA Technologies, IA). The nucleic acid with the sequence of interest is suspended in 1×TE to give a 60 μM probe concentration. The final composition of nucleic acid microparticles can be 18% PEG-DA 700, 36% PEG 200, 35% 3×TE, 6.5% 1×TE and 4.5% Darocur. For antibodies, they can be PEGylated and mixed with the PEG matrix. This includes combining antibodies at 25 μg/μL antibody in PBS with 50 μg/μL heterobifunctional PEG linker at a 4:1 (vol/vol) ratio and functionalizing at room temperature on a shaker at 1000 r.p.m, and incubated for 3 h. The PEGylated antibodies are mixed with 20% pre-polymer mixture at a 1:9 (vol/vol) ratio. The solution is vortexed vigorously and then centrifuged prior to use. Other types of biomolecules can be immobilized in the PEG matrix in a similar manner.

To control the size and shape of the microparticles, the photomask pattern is changed. The simplest shape is rectangular, but a wide variety of different elongated shapes can be synthesized to maintain the length measurement of the microparticles. Example dimensions of microparticles are included in Table 1. In this example, there are three different lengths and four different relative dye concentrations, resulting in twelve different combinations. Additional length and dye combinations can be included, including the use of a second dye color for additional multiplexing.

TABLE 1

Example dimensions of microparticles.

| Particle ID | Width (μm) | Depth (μm) | Length (μm) | [Dye] |
|---|---|---|---|---|
| 1 | 20 | 20 | 120 | 1x |
| 2 | 20 | 20 | 90 | 1x |
| 3 | 20 | 20 | 60 | 1x |
| 4 | 20 | 20 | 120 | 3x |
| 5 | 20 | 20 | 90 | 3x |
| 6 | 20 | 20 | 60 | 3x |
| 7 | 20 | 20 | 120 | 6x |
| 8 | 20 | 20 | 90 | 6x |
| 9 | 20 | 20 | 60 | 6x |
| 10 | 20 | 20 | 120 | 9x |
| 11 | 20 | 20 | 90 | 9x |
| 12 | 20 | 20 | 60 | 9x |

Data analysis is performed with custom software. Poisson photon counting statistics are assumed:

$$f_p(x) = \frac{e^{-a}a^x}{x!} \quad \text{(Eq. 2)}$$

2 here x is the value, p is the probability, a is the mean, and the standard deviation σ is √a. Relative microparticle length is determined by the time of transit through the first laser and measuring the full width at half maximum (FWHM) of each. Burst intensity is determined by integrating the area under the curve for each peak. Mean peak intensity is determined by the burst intensity divided by peak width.

Figure 5:
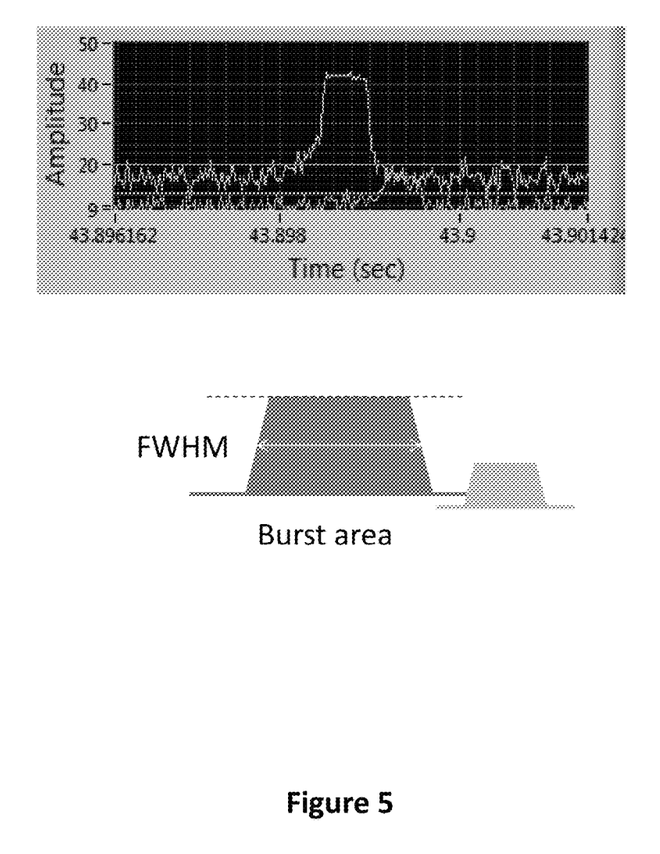
FIG. 5 shows the fluorescence versus time data trace for a rectangular microparticle passing through the system in accord with the present invention.

FIG. 5 shows the fluorescence versus time data trace for a rectangular microparticle passing through the system. The first plateau signal codes for the microparticle and the second signal represents the measured analyte intensity. The full-width half maximum (FWHM) is utilized to determine the relative lengths of the microparticles and the burst or mean intensity is utilized to measure the dye concentration.

The microparticles are grouped by length, defined by the rising and falling edges of the data traces, and also the total microparticle burst intensity. The grouping is automatic and based on k-means clustering. k is equal to the number of clusters, with one mean per cluster. An initial condition is assigned and then iterated until the means are moved to the center of the clusters. The main goal of the algorithm is that it minimizes the objective function:

$$J = \sum_{j=1}^{k}\sum_{i=1}^{n}\left\|x_i^{(j)} - c_j\right\|^2 \quad \text{(Eq. 3)}$$

Where $\|x_i^{(j)}-c_j\|^2$ is a chosen distance measure between a data point $x_i^{(j)}$ and the cluster centre $c_j$, is an indicator of the distance of the n data points from their respective cluster centres. The initial condition of the algorithm is important and is set to where the microparticle clusters are expected.

After the clustering is complete, the orange fluorescence values for each cluster are determined. This includes the mean, standard deviation, and coefficient of variation. These values are automatically recorded for each cluster for each standard and sample.

Figure 6:
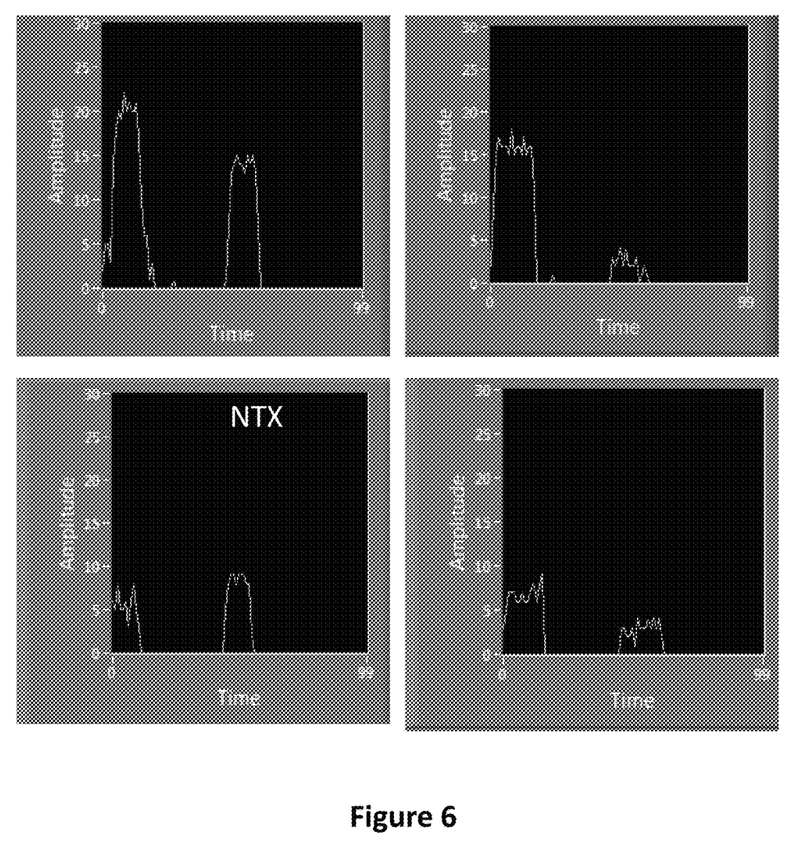
FIG. 6 shows the laser-induced fluorescence readout of four different microparticles multiplexed by length and dye intensity in accord with the present invention.

FIG. 6 shows laser-induced fluorescence readout of four different microparticles multiplexed by length and dye intensity. The y-axes on the images are fluorescence intensity and the x-axes represent time. There are two signal traces in each of the charts, one preceding the other. The first plateau is blue fluorescence and the second signal plateau is the assay orange fluorescence. The multiplexing is based off the blue fluorescence. The blue fluorescence intensity and length, as determined by the full-width half maxima, code for each of the assays.

Figure 7:
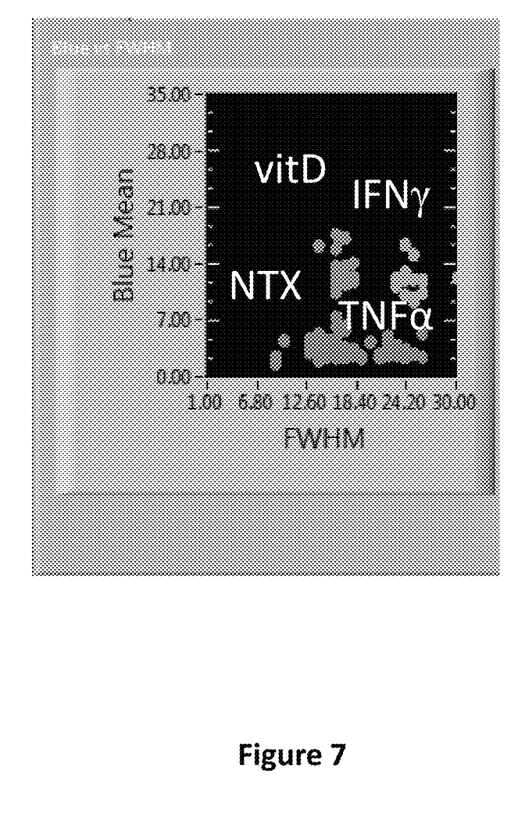
FIG. 7 shows a plot of fluorescence intensity versus the FWHM.

FIG. 7 shows four populations on a graph plotting the blue mean fluorescence intensity versus the FWHM. Four distinct populations are evident in the image. Each one of the populations corresponds to one assay.

Those skilled in the art will recognize, or be able to ascertain using no more than routine experimentation and/or engineering, many equivalents to the specific embodiments of the invention described herein. The scope of the present invention is not intended to be limited to the above Description, but rather is as set forth in the claims that follow the reference list.

What is claimed is:

1. A microparticle comprising:
    at least two elements, wherein each element has its own length and its own dye concentration, and the length of the first element is approximately an integer multiple of the length of the second element,
    wherein the microparticle is elongated and the integer is greater than one,
    wherein the microparticle has an axis passing through every length of each element in the microparticle, and
    wherein any planar cross-section of the microparticle perpendicular to the axis is homogenous and uniformly responds to laser radiation.

2. The microparticle of claim 1, wherein each of the at least two elements incorporates a different fluorescent dye.

3. The microparticle of claim 1, wherein the microparticle is fabricated substantially from polyethylene glycol.

4. The microparticle of claim 1, wherein the length of each of the at least two elements is at least the length required for a reader to identify a change in the element.

5. The microparticle of claim 1, wherein the microparticle is rectangular in shape.

6. The microparticle of claim 1, wherein the microparticle is cylindrical in shape.

7. A method for conducting an assay, the method comprising:
    introducing at least one microparticle into a sample, the microparticle comprising at least one element, wherein each element has its own length and its own dye concentration, the microparticle is elongated, the microparticle has an axis passing through the longest length of each element in the microparticle, and any planar cross section of the microparticle perpendicular to the axis is homogenous and uniformly responds to laser radiation;
    scanning the at least one microparticle with a laser; and
    grouping the microparticle by at least one of length or burst intensity.

8. The method of claim 7, wherein scanning the at least one microparticle with a laser determines the length of the at least one microparticle and provides a scanning measurement, and the method further comprises:
    integrating the scanning measurement to determine burst intensity; and
    grouping the microparticle by its length and burst intensity.

9. The method of claim 7, further comprising increasing the speed of the scanning with the laser.

10. The method of claim 7, wherein the microparticle is rectangular or cylindrical in shape.

11. The method of claim 8, wherein the grouping of the microparticles is based on k-means clustering.

12. An assay system comprising:
    a source of elongated microparticles, each microparticle comprising at least two elements, wherein each element has its own length and its own dye concentration, and the length of the first element is approximately an integer multiple of the length of the second element and the integer is greater than one; and
    a scanning laser connected to a processing unit configured to group the microparticles by at least one of scanned length or burst intensity.

13. The system of claim 12 wherein the processing unit is configured to:
    control the laser to determine the length of at least one microparticle;

integrate the scanning measurements to determine burst intensity; and group the microparticles by their length and burst intensity.

14. The system of claim 13 wherein the processing unit is configured to control the sampling rate by which the laser determines the length of at least one microparticle.

15. The system of claim 12, wherein each of the at least two elements of the microparticles incorporates a different fluorescent dye.

16. The system of claim 12, wherein the microparticles are rectangular in shape.

17. The system of claim 12, wherein the microparticles are cylindrical in shape.

* * * * *